United States Patent [19]

McGredy

[11] Plant 4,694

[45] Apr. 21, 1981

[54] NEW ROSE PLANT

[76] Inventor: Samuel D. McGredy, P.O. Box 14-100, Auckland, New Zealand

[21] Appl. No.: 114,976

[22] Filed: Jan. 24, 1980

[51] Int. Cl.[3] ..... A01H 5/00

[52] U.S. Cl. ..... Plt./20

[58] Field of Search ..... Plt./20

*Primary Examiner*—James R. Feyrer

*Attorney, Agent, or Firm*—Vincent G. Gioia

[57] ABSTRACT

A new hybrid tea rose variety of vibrant currant red coloring, substantially non-fading and long lasting on the plant and as a cut flower.

1 Drawing Figure

The present invention relates to a new and distinct variety of rose plant of the hybrid tea rose class, which was originated by my crossing as seed parent the rose known as "John Waterer" and the rose known as "Kalahari" as pollen parent.

Among the novel characteristics possessed by this new variety which distinguish it from its parents and all other varieties of which I am aware are vibrant, substantially non-fading, currant red, high centered, singly borne blooms, developing from long pointed buds and a vigorous, free branching plant with abundant foliage and superior disease resistance. Flowers are exceptionally long lasting on the plant and as a cut flower. Asexual reproduction by budding of the new variety as performed in Clackamas County, Oreg., shows that the foregoing and other distinguishing characteristics come true to form and are established and transmitted through succeeding propagations.

The new and improved rose variety which I have developed is an unusually fine hybrid tea rose with singly-borne blooms of high centered, excellent hybrid-tea form displayed on a vigorous upright, free branching plant with abundant disease resistant foliage. The flowers are of medium petalage and have a moderate spicy fragrance. The brilliant red coloring holds well upon aging.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "46A" is plate 46A of the Royal Horticultural Society Color Chart.

Parentage: Seedling.

*Seed parent.*—"John Waterer".

*Pollen parent.*—"Kalahari".

Class: Hybrid tea.

The following observations are made of specimens grown outdoors in Clackamas County, Oreg. during the month of September.

1. FLOWER

Blooming habit: Continuous.

A. *Bud.*—(1) Size: Medium. (2) Form: Long pointed. (3) Color: When sepals first divide—46A. When petals begin to unfurl—46A to 46B. (4) Sepals: Simple, occasionally fancy, about same length as bud. (5) Peduncle: Length—medium. Aspect—straight. Strength—erect. Color—reddish green 16A.

B. *Bloom.*—(1) Size: Average size when fully expanded—about 4-inches. (2) Borne: Primarily singly. (3) Form: High centered slightly flaring. (4) Petalage: Number of petals under normal conditions—about 24. (5) Color: (during first two days). Petal coloring both top and underside surfaces is generally 46A to 46B, newly unfurled petals have velvet texture adding to vibrancy of the coloring. Color does not change greatly upon aging so that general tonality from a distance remains vibrant red.

C. *Petals.*—(1) Texture: Thick. (2) Appearance: Velvety to satiny. (3) Form: Acuminate. (4) Arrangement: Regularly arranged. (5) Petaloids in center: Few. (6) Persistence: Drop off cleanly. (7) Fragrance: Moderate spicy. (8) Lasting quality: Very long lasting on plant and as cut flower.

2. REPRODUCTIVE ORGANS

A. Stamens, filaments and anthers:

(1) *Arrangement.*—Regular, slightly incurved.

(2) *Color.*—162A.

B. Pollen: Color—163B.

C. Styles: Uneven, hairy.

D. Stigmas: Color—9C.

E. Hips:

*Shape.*—Long, ovoid.

*Size.*—Small.

*Color.*—Green with reddish tone.

*Do seeds protrude?.*—Yes and styles persist.

3. PLANT

A. Form: Upright.

B. Growth: Vigorous, free branching.

*Height attained.*—About 4½ feet.

C. Foliage: Compound 5 to 7 leaflets, noticeable proportion of 5-leaflet leaves.

(1) *Size.*—Large.

(2) *Quantity.*—Abundant.

(3) *Color.*—New foliage: Upper side—near to 59C. Under side—near to 60C. Old foliage: Upper side—136A. Under side—139C.

(4) *Shape.*—Ovoid, acuminate.

(5) *Texture.*—Upper side is glossy and under side is dull.

(6) *Edge.*—Serrated.

(7) *Serration.*—Simple.

(8) *Leaf stem.*—Color—near to 139B. Under side—139C.

(9) *Stipules.*—Long.

(10) *Resistance to disease.*—Blackspot—excellent. Mildew—excellent. Rust—excellent.

D. Wood:

(1) *New wood.*—Color—near 59A. Bark—smooth, shiny.

(2) *Old wood.*—Color—near 138A. Bark—smooth, shiny.

E. Thorns:

(1) *Thorns.*—Quantity (main stalk): ordinary. On laterals from stalk—few. Form—recurved. Length—medium. Color—138A. Position—scattered.

(2) *Prickles.*—Few.

F. Winter hardiness: Good winter hardiness.

I claim:

1. A new and distinct variety of rose plant of the hybrid tea class, substantially as shown and described, characterized particularly by high centered, flowers of persistent currant red coloring borne primarily singly to a stem and are long lasting on the plant and as cut flowers.

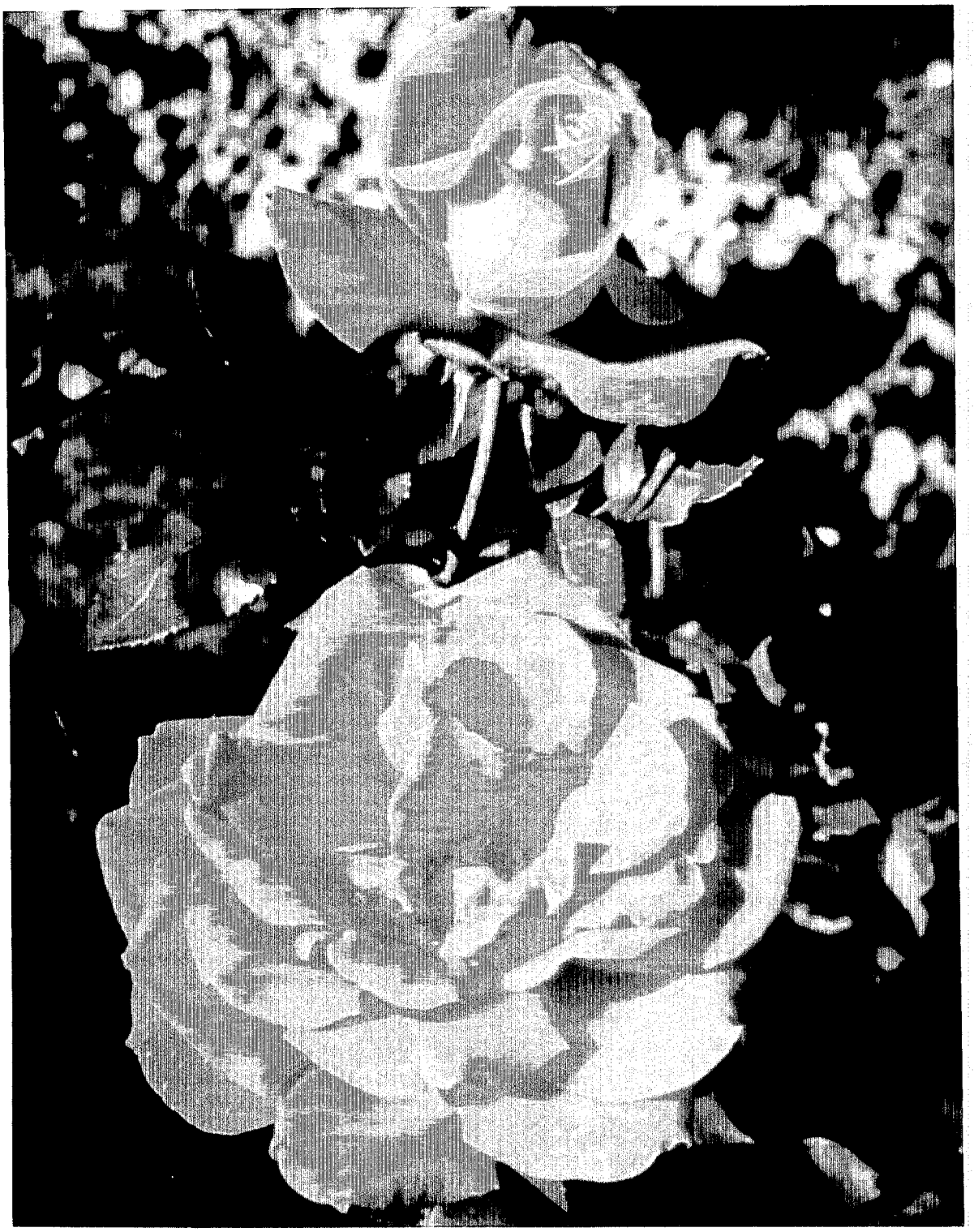

* * * * *